United States Patent

Naab et al.

Patent Number: 4,904,789
Date of Patent: Feb. 27, 1990

[54] PROCESS FOR THE PREPARATION OF UNSYMMETRICAL DIHYDROPYRIDINES

[75] Inventors: Paul Naab; Willi Lange; Werner Teller, all of Wuppertal, Fed. Rep. of Germany

[73] Assignee: Bayer Aktiengesellschaft, Leverkusen, Fed. Rep. of Germany

[21] Appl. No.: 275,301

[22] Filed: Nov. 23, 1988

[30] Foreign Application Priority Data

Dec. 8, 1987 [DE] Fed. Rep. of Germany ....... 3741540

[51] Int. Cl.$^4$ ........................................... C07D 211/02
[52] U.S. Cl. ................................................... 546/321
[58] Field of Search ........................................ 546/321

[56] References Cited

FOREIGN PATENT DOCUMENTS 2117571 10/1972 Fed. Rep. of Germany .
2117573 10/1972 Fed. Rep. of Germany .

Primary Examiner—Mary C. Lee
Assistant Examiner—J. Haley
Attorney, Agent, or Firm—Sprung Horn Kramer & Woods

[57] ABSTRACT

In the preparation of nitrenedipine by reaction of an ylidene compound of the formula

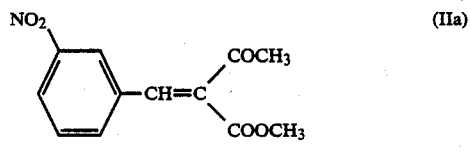

or

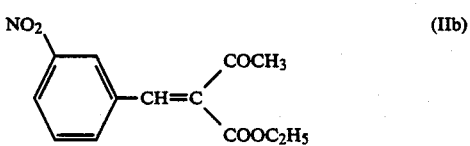

with an enamine compound of the formula

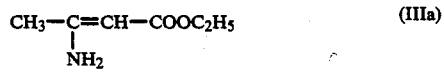

or

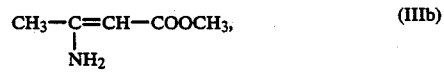

the improvement which comprises effecting the reaction in the presence of a catalytic amount of diisopropylamine acetate or dimethylbenzylamine acetate. The product is produced in high yield with reduced amounts of symmetrical by-products.

4 Claims, No Drawings

PROCESS FOR THE PREPARATION OF UNSYMMETRICAL DIHYDROPYRIDINES

The present invention relates to a chemically original process for the preparation of unsymmetrical 1,4-dihydropyridine carboxylic acid esters.

The compound methyl ethyl 4-(3-nitrophenyl)-2,6-dimethyl-1,4-dihydropyridine-3,5-carboxylate (referred to as nitrendipine below) is already known from German Offenlegungsschrift 2,117,571 as are the processes for their preparation (compare also German Offenlegungsschrift 2,117,573). The preparation of unsymmetrical dihydropyridines by the reaction of xlidene compounds with enaminocarboxylic acid esters is likewise described in EPA-O,124,743. In EP-Application 0,124,743, the ylidene compounds to be employed are obtained in particular purity and yield by the use of certain catalysts, which should again lead to very pure final products on further reaction to give dihydropyridines.

Nitrendipine is an acknowledged pharmaceutically active compound which is already legally permitted as a medicament in numerous countries and is used medicinally. The necessity for particular purity exists for pharmaceutically active compounds of this type. In the preparation of unsymmetrical dihydropyridines, and in particular in the preparation of nitrendipine, symmetrical esters which, as undesired by-products, can only be separated from the correwsponding unsymmetrical esters in a troublesome and costly manner, hitherto also always result to a considerable extent in addition to the desired active compound (compare the following formula diagram).

Nitrendipine
(unsymmetrical esters)

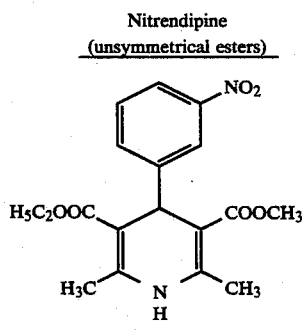

I

Symmetrical esters
(undesired by-products)

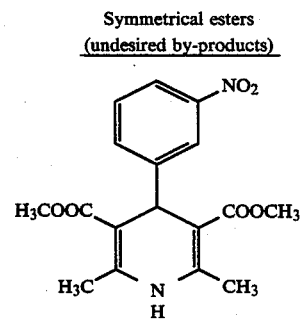

A

-continued

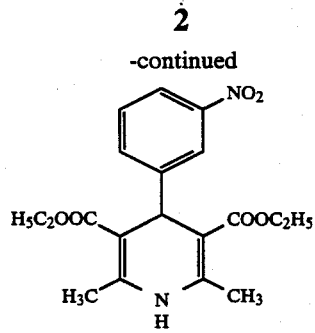

B

The invention relates to a process for the preparation of nitrendipine by reaction of an ylidene compound of the general formula II (IIa) or (IIb)

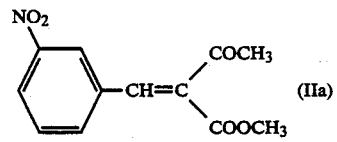

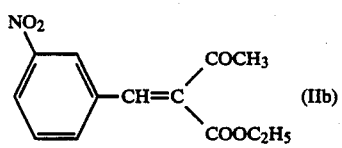

with an enamine compound of the general formula III (IIIa) or (IIIb)

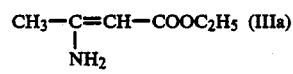

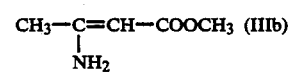

characterized in that the reaction is carried out in an organic solvent in the presence of catalytic amounts of diisoporpylamine acetate r dimethylbenzylamine acetate.

Aliphatic alcohols having 1 to 6 C atoms, in particular methanol, ethanol and/or isopropanol are preferably used as organic solvents.

The reaction is preferably carried out at tempertures between $-10$ and $150°$ C., in particular between 40 and $100°$ C.

The catalyst is preferably employed in amounts from 0.001 to 0.009 mol, in particular from 0.003 to 0.008 mol, per mol of ylidene compound.

It has surprisingly been found that the ring closure of ylidene compound and enamines by the use of catalysts according to the invention proceeds, in particular in compliance with the concentration data mentioned, in very high yields (more than 90% of theory) and at the same time only extremely low amounts of undesired symmetrical esters are formed. Moreover, the reaction time is substantially shorter in comparison to the previously known methods. The reaction is, as a rule, finished after only a few hours.

To demonstrate the unexpected advantage of the process according to the invention, the preparation of nitrendipine was repeated according to the exemplary embodiments of EP-A-O,124,743. By combination of Examples 1 and 2, nitrendipine was obtained in a yield of about 80% of theory (m.p.: 159° C.). A thin-layer chromatographic investigation on Merck silica gel plates (mobile phase: chloroform:acetone:petroleum ether =3:2: 5) showed no evident by-products.

A chromatographic investigation by means of HPLC (for example Hibar ready-made column, Merck, Darmstadt) (column: length 12.5 cm, dia. 4 mm, filling LiChrosorb RP 18, 5 μm. Eluent: acetonitrile/tetrahydrofuran/water =120/240/640 (V/V). Flow rate: 1.5 ml/min. Detector wavelength: 235 nm. Relative retention times: nitrendipine 1.00; symmetrical ester A 0.75,symmetrical ester B 1.35.) shows, however, that the nitrendipine obtained was strongly contaminated by symmetrical esters. 2.64% of the methyl ester (formula A) and 2.55% of the ethyl ester (formula B) were detected as impurities. Even after repeated recrystallization from methanol in the presence of activated charcoal (crystallization yield about 85%), the symmetrical by-products A and B were detected in an amount of 2.27% and 2.34% on fresh HPLC investigation. This crystallization test at the same time shows the difficulty of separating the symmetrical by-products from nitrendipine.

The following exemplary embodiment shows, by way of example, the rate of the process according to the invention, its high yield and the unexpectedly low amount of undesired symmetrical compounds.

EXAMPLE 1

45 g (0.39 mol) of methyl aminocrotonate, 92.5 g (0.35 mol) of ethyl 3-nitrobenzylideneacetoacetate (prepared from ethyl acetoacetate and 3-nitrobenzaldehyde) are heated to boiling with 2.5 ml of a 10% strength solution of dimethylbenzylamine acetate (desmorapid acetate in the following; prepared from the corresponding acetic acid and dimethylbenzylamine in isopropanol and diluted to 100 ml; ≙1.3 mmol) in 275 ml of isopropanol and stirred at reflux for 5 hours. In this way, a total of 500 ml of isopropanol are emoved by distillation and replaced again by fresh solvent. The batch is cooled to 50° C., seeded with nitrendipine and stirred overnight at room temperature. It is then cooled to 0°-5° C., stirred for 2 hours at this temperature, filtered off with suction, washed with 90 ml of methanol and dried overnight invacuo at 40° C. Yield: 121.1 g (≙96% of theory)

By HPLC, 0.13% of the symmetrical ester A can be detected. The content of the symmetrical ester B is under 0.05%.

It will be appreciated that the instant specificationand claims are set forth by way of illustration and not limitation, and that various modifications and changes may be made without departing from the spirit and scope of the present invention.

What is claimed is:

1. In the preparation of nitrendipine by reaction of an ylidene compound of the formula

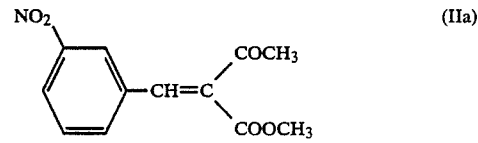

or

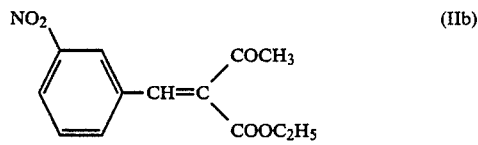

with an enamine compound of the formula

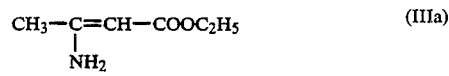

or

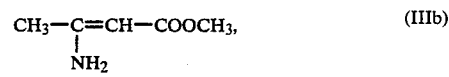

the improvement which comprises effecting the reaction in the presence of a catalytic amount of diisopropylamine acetate or dimethylbenzylamine acetate.

2. A process according to the claim 1, wherein the reaction is effected in an aliphatic alcohol having up to 6 carbon atoms as a solvent.

3. A process according to claim 1, wherein the reaction is effectted between about −10 and 150° C.

4. A process according to claim 1, wherein the reaction is carried out in the presence of about 0.001 to 0.009 mol of the catalyst per mol of ylidene compound II.

* * * * *